(12) United States Patent
Gouman et al.

(10) Patent No.: US 8,802,872 B2
(45) Date of Patent: Aug. 12, 2014

(54) PROCESS FOR PREPARING GLYCIDYL ESTERS OF BRANCHED MONOCARBOXYLIC ACIDS

(75) Inventors: Jan Gouman, Barendrecht (NL); Sandra Rens-van der Lee, Rhoon (NL); Robert van t Sand, Spijkenisse (NL)

(73) Assignee: Momentive Specialty Chemicals Inc., Columbus, OH (US)

( * ) Notice: Subject to any disclaimer, the term of this patent is extended or adjusted under 35 U.S.C. 154(b) by 110 days.

(21) Appl. No.: 13/377,470

(22) PCT Filed: Jun. 2, 2010

(86) PCT No.: PCT/EP2010/003334
§ 371 (c)(1),
(2), (4) Date: Jan. 4, 2012

(87) PCT Pub. No.: WO2010/142396
PCT Pub. Date: Dec. 16, 2010

(65) Prior Publication Data
US 2012/0095244 A1    Apr. 19, 2012

(30) Foreign Application Priority Data
Jun. 11, 2009  (EP) ..................... 09075264

(51) Int. Cl.
*C07D 301/27* (2006.01)

(52) U.S. Cl.
USPC ......................................... 549/515

(58) Field of Classification Search
USPC ......................................... 549/515
See application file for complete search history.

(56) References Cited

U.S. PATENT DOCUMENTS

| | | | |
|---|---|---|---|
| 2,992,239 A | | 7/1961 | Nevin et al. |
| 3,075,999 A | | 1/1963 | June et al. |
| 3,178,454 A | * | 4/1965 | Kloos ........................... 549/515 |
| 3,275,583 A | | 9/1966 | Kloos |
| 3,859,314 A | | 1/1975 | Dukes et al. |
| 6,570,028 B1 | | 5/2003 | Heymans et al. |
| 2010/0180802 A1 | | 7/2010 | Gumlich et al. |

FOREIGN PATENT DOCUMENTS

| | | |
|---|---|---|
| CN | 1425729 | 6/2003 |
| CN | 101085764 | 12/2007 |
| CN | 101245033 | 2/2008 |
| CN | 101245053 | 8/2008 |
| DE | 1219481 | 6/1966 |
| DE | 2127699 | 12/1972 |
| EP | 0475238 A2 | 3/1992 |
| EP | 822189 | 2/1998 |
| EP | 1115714 B1 | 7/2001 |
| GB | 763559 | 12/1956 |
| GB | 1058075 A | 2/1967 |
| JP | S44004971 B | 2/1969 |
| JP | S47043529 B | 11/1972 |
| JP | S49000815 B | 1/1974 |
| JP | S49054329 A | 5/1974 |
| JP | S53147018 A | 12/1978 |
| JP | S57130980 A | 8/1982 |
| JP | 57203077 | * 12/1982 |
| JP | H04279624 A | 10/1992 |
| JP | H05078340 A | 3/1993 |
| JP | 2003171371 A | 6/2003 |
| WO | WO 2009/000839 | 12/2008 |

* cited by examiner

*Primary Examiner* — Taylor Victor Oh

(57) ABSTRACT

Accordingly, the invention relates to a process for the preparation of a glycidyl ester of a branched monocarboxylic acid by reacting an aliphatic monocarboxylic acid of the formula $R^1R^2R^3CCOOH$, wherein $R^1$, $R^2$, and $R^3$ each independently represent an alkyl radical of normal or branched structure containing from 1 to 20 carbon atoms and an epoxyalkyl halide containing from 3 to 13 carbon atoms in the presence of a catalyst, wherein a greater than stoichiometric amount of epoxyalkyl halide is reacted with the acid (e.g., preferably in the molar ratio of epoxyalkyl halide to acid that is in the range of from 1.02:1 to 1.50:1) to form an intermediate reaction product comprising a halohydrin, the epoxyalkyl halide is added to the acid with appropriate cooling of the reactants and/or the reaction mixture to keep the temperature of the reaction mixture below 80° C., whereupon the epoxyalkyl halide and the acid are reacted at a temperature below 80° C. (preferably in the range of from 55 to 75° C.) for a time sufficient to reduce the amount of acid to no more than 2 wt % but no less than 0.1 wt % calculated on the initial amount of acid, optionally removing any excess epoxyalkyl halide from the reaction product prior to the ring closure reaction, subjecting the reaction product to a ring closure reaction (DHC) and optionally to one or more after treatments (ADHC) for removal of any remaining halo functionality.

20 Claims, No Drawings

PROCESS FOR PREPARING GLYCIDYL ESTERS OF BRANCHED MONOCARBOXYLIC ACIDS

This application claims the benefit of PCT Application PCT/EP2010/003334 with International Filing Date of Jun. 2, 2010, published as WO 2010/142396 A1, which further claims priority to European Patent Application No. 09075264.3 filed Jun. 11, 2009, the entire contents of both are hereby incorporated by reference.

TECHNICAL FIELD

The current invention concerns a process for preparing glycidyl esters by reacting a carboxylic acid, in particular a secondary or tertiary branched monocarboxylic acid (alpha-branched or alpha,alpha-dialkyl carboxylic acid) containing at least 5 carbon atoms, and an epoxyalkyl halide, i.e., a compound having an oxirane group that is joined directly to an aliphatic carbon atom bearing a halogen atom, in the presence of a catalyst. More in particular the present invention relates to a process for preparing glycidyl esters of α-branched monocarboxylic acids containing from 5 to 20 carbon atoms and preferably from 9 to 13 carbon atoms.

BACKGROUND ART

Glycidyl esters of α-branched monocarboxylic acids are useful for the preparation of epoxy, acrylic polyester and alkyd resins, either directly or via intermediate products such as adducts with (meth)acrylic acid amines, polyols and polyacids or as reactive diluents for the preparation of thermoset acrylic, epoxy polyester and/or urethane paints and coatings. Of particular interest are glycidyl esters of aliphatic monocarboxylic acids represented by the formula

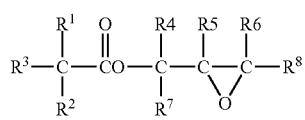
(1)

wherein $R^1$, $R^2$ and $R^3$ each represent the same or different alkyl radicals of normal or branched structure containing 1-20 carbon atoms, and $R^4$ through $R^8$ each represent hydrogen or a hydrocarbyl group containing 1-3 carbon atoms. A more preferred product is one where $R^1$ through $R^3$ are alkyl groups containing a sum total of 3-18 carbon atoms and where $R^4$ through $R^8$ are each hydrogen, e.g., the reaction product of neodecanoic acid ($R^1+R^2+R^3$=C8) and epichlorohydrin.

The preparation of epoxy esters or also called glycidyl esters by reacting a mono- or polycarboxylic acid with an epoxyalkyl halide, such as epichlorohydrin, is well known. The process may be carried out in a single step with an alkali metal salt of the acid, as disclosed in U.S. Pat. No. 3,178,454. It should be realized, however, that many of the acids converted into glycidyl esters are soap-forming acids, with complicated preparation steps. The complications are due to foaming phenomena during water evolution. Moreover, there are problems in respect of caking and stirring complications due to the high viscosity of soap gel. This invention does not concern the process using a metal salt of the acid.

The epoxy esters may also be made by reaction of the carboxylic acid with epoxyalkyl halide. This reaction involves the coupling of the epoxyalkyl halide to the acid group, whereby a halohydrin ester intermediate is formed. This is then followed by a second step involving a ring closure reaction (DHC). Typically, the reaction is then followed by one or more after treatments (ADHC) for the removal of any remaining halo functionality.

In U.S. Pat. No. 3,075,999 the process for the preparation of glycidyl esters of fatty acids is described. It comprises contacting an acid with an excess epoxyalkyl halide (an unsubstituted 1-halo-2,3-epoxyalkane of from 3 to 13 carbon atoms), in the presence of a catalyst at a temperature of 70 to 117° C. (boiling point of epichlorohydrin) while adding thereto an aqueous solution of an alkaline compound. The preferred catalyst is tetramethyl ammonium bromide and the preferred epoxyalkyl halide is epichlorohydrin (ECH). The equivalent ratio of ECH to acid may range from 15:1 to 2:1. In a typical experiment a tenfold excess of ECH is used, calculated on the acid. An equimolar amount of potassium hydroxide is added at reflux conditions and excess ECH and water are separated overhead. The products produced by this process have an Epoxy Group Content (EGC) of around 0.25 equivalent/100 g. This corresponds with a purity of around 87.5% (calculated on the actual EGC, divided by the theoretical EGC times 100%). They are produced at a reasonable high yield of 97% (calculated on the mol product divided by the mol acid times 100%). Although more then 40 years old, this process remains very attractive because of its simplicity. For instance, the water phase can be easily separated from the overhead and the excess ECH can be easily reused without the need for additional distillation steps and such. On the other hand, the EGC and hence the purity is low. It may be possible to improve the EGC by purifying the product, but this is at the detriment of the yield.

It is therefore the aim of the current invention, to find a process that is similar to this U.S. Pat. No. 3,075,999 process, but that yields glycidyl esters of branched monocarboxylic acids with a significantly higher EGC, in other words with a purity of at least 93.5%, preferably at least 94% and at a yield that is at least 95%, preferably at least 98% based on the starting fatty acid.

In CN 101245053 a method is disclosed for the preparation of neodecanoic acid glycidyl ester. The process involves dripping the neodecanoic acid (a mixture primarily composed of 2-ethyl-2,5-dimethylhexanoic acid) into a mixture of ECH, sodium hydroxide and catalyst, that is heated to 90° C. According to this reference, the reaction cycle is said to be short, the reaction yield is high, and the yield to be about 86 percent. However, upon study of this case, the current inventors found that the preparation method is not better than the old process of the US '999 reference. Thus, despite all recent developments, a need remains to improve the process for making glycidyl esters of branched monocarboxylic acids.

Interestingly, in WO 00/17179 a process is described for the preparation of glycidyl esters of alpha-branched monocarboxylic acids with a higher EGC. Again an epoxyalkyl halide is used in a molar excess (2-20, preferably 3-20, calculated on the acid). The reaction is carried out in the presence of a solvent and at a temperature in the range of from 30 to 110° C., preferably in the range from 65 to 95° C. A wide range of catalysts may be used, including alkali metal hydroxides, alkali metal carbonates, alkaline earth hydroxides, alkali metal or alkaline earth metal alcoholates; ammonium salts; and phosphonium halides, with alkali metal hydroxides and alkali metal alkanoates being preferred. A solvent, preferably an alkanol, is used to enable the dissolution of the catalyst of step (a). For instance, in Example 1 of this reference, a glycidyl ester is produced with an EGC of 4210 mmol/kg (i.e., purity of 96.2%), at a 96% yield, using a process involving isopropanol as solvent and fourfold excess of ECH. NaOH is added in a minor amount first, followed by cooling down and phase separation. After the subsequent alkali dosing the reaction product is separated again, into an aqueous phase and an organic phase. From this phase the excess ECH is removed by steam distillation and the product is treated with NaOH solution to convert the remaining hydrolysable chlorine. The organic phase is washed several times with water whereupon the organic phase is stripped with steam and dried. Without washing, as shown in Example 2 of this reference, the hydrolysable chlorine content increases. Without solvent, as shown in comparative example (a) of this reference, the hydrolysable chlorine content is even more than 5 times greater, whereas the EGC is only 2675 mmol/kg. From this reference it would therefore appear that a solvent is essential in order to reach a high EGC.

This reference, however, is silent as to the aspect of solvent removal and the energy requirements to distil said solvent. Interestingly, as shown in examples 6 to 11, the use of calcium hydroxide, tetramethyl ammonium chloride (TMAC) or ethyl triphenyl phosphonium iodide resulted in large amounts of residual acid and the salt thereof; the preparation of a glycidyl ester must therefore have been very limited, if any at all. This process has as a disadvantage that a solvent is required that must be removed during the process. The aim of the current inventors, on the other hand, is to improve the U.S. Pat. No. 3,075,999 process and to achieve an EGC similar to that in WO 00/17179, but without use of a solvent which adversely affects the economics of the process.

In CN 101085764 a method is disclosed for synthesizing (methyl)acroleic acid glycidic glyceride. It takes (methyl) glyceride as raw material, and reacts this with epichlorohydrin for ring opening and esterification under catalyst and inhibitor action. It then carries out ring-closure reaction with caustic soda to prepare (methyl)acroleic acid glycidic glyceride. Advantages of this method include low consumption of epichlorohydrin, no utilization of organic solvent during reaction, short process, simple operation, easy industrialization and little environmental pollution. The molar ratio of ECH to acid in the coupling reaction is 1-1.4:1. The temperature may vary from 60-100° C. An epoxy value of 0.503 eq/100 g is obtained, which corresponds with a purity of 71.4%. This is therefore a rather low EGC. Also the yield is rather poor: at about 26%. It would therefore seem that the process used in this reference is of little interest. Moreover, this reference does not concern the preparation of glycidyl esters of aliphatic branched monocarboxylic acids having at least 5 carbon atoms. The problem of purity and yield is not specifically addressed and specific measures to yield epoxy esters with an improved EGC at high yield are not as such mentioned.

EP 822189 A concerns a method for producing purified epoxy compound. Thus an epihalohydrin or 2-methylepihalohydrin is reacted with a compound having 2-4 carboxyl groups or 1-3 amido groups in the compound. Products are obtained at about 41% purity and 92% yield (example 1). This reference, once again, does not concern the preparation of glycidyl esters of aliphatic branched monocarboxylic acids having at least 5 carbon atoms. The problem of (relatively) low EGC is not encountered. Thus, specific measures to yield epoxy esters with an improved EGC at high yield are not as such mentioned.

JP 2003171371 concerns a method for producing alpha-monobranched saturated carboxylic glycidyl esters. The alpha-monobranched saturated aliphatic carboxylic glycidyl ester is produced by ring-opening reaction the acid and epihalohydrin in the presence of a catalyst and by ring-closing reaction of the halohydrin ester by using a dehydrohalogenation agent. Any excess epihalohydrin is removed before the product is treated with the dehydrohalogenation agent. The molar ratio of ECH to acid in the coupling reaction is 1.5-5.0:1, with all examples using an ECH at a molar ratio greater than 1.5. The temperature may vary from 30-120° C., whereas in the examples a temperature of about 80° C. is used. Although this application does address the issue of undesirable side-reactions, there remains a need for further improvement, in particular in respect of the yield and purity of the final glycidyl ester.

EP 475238 A concerns glycidyl esters of mono- and polycarboxylic acids containing one or more mesogenic moieties, curable compositions and cured compositions thereof. These glycidyl esters exhibit ordering of the molecular chains in the melt phase and/or in the advanced compositions thereof. This morphology is susceptible to orientation during processing which can result in enhanced unidirectional mechanical properties. In for instance example F, products are made at a purity of about 73% and a yield of about 74%. This reference does not concern the preparation of glycidyl esters of aliphatic branched monocarboxylic acids having at least 5 carbon atoms. Once again, specific measures to yield epoxy esters with improved purity at high yield are not as such mentioned.

According to DE 2127699 hydrolysis resistant glycidyl esters are prepared by catalytic reaction of mono- and/or polycarboxylic acids containing at least 1 carboxyl group bound to a tertiary or quaternary C-atom and epichlorohydrin, using 1-1.15 mol. epichlorohydrin to 1 carboxyl group equivalent, using water as reaction medium, followed by treatment with aq. alkali. The addition of the epichlorohydrin is carried out at a temperature of from 80-110° C., whereas in the examples a temperature of from 96 to 105° C. is used. The EGC is high, but at the detriment of the yield. In example 4 an "Epoxidzahl" of 18.7 is achieved. This corresponds to a purity of 98.7%. On the other hand, the yield is at most 95% or likely lower due to the distillation steps.

According to JP 57203077 a carboxylic acid and a little excessive amount of epichlorohydrin are heated to effect reaction to form a chlorohydrin ester, then the unreacted epichlorohydrin is recovered in the presence of an aqueous alkali and the dehydrochloric cyclization reaction is effect to give an alpha branched saturated fatty acid glycidyl ester. More specifically, a small amount of aqueous alkali is added to the reaction mixture and heated under reduced pressure to convert dichlorohydrin, a by-product, into epichlorohydrin which is distilled off azeotropically. Then, the remaining chlorohydrin ester is combined with an aqueous alkali and heated to effect dehydrochloric cyclization to give the titled substance. The molar ratios of epichlorohydrin to carboxylic acid in the two examples are 1.3:1 and 1.5:1. The preferred temperature for the coupling reaction is 70-140° C., whereas in the examples a temperature of 90 and 120° C. is used. A suggestion to improve the purity at high yield is not provided.

In JP 57130980 epoxyalkyl esters are prepared of branched carboxylic acids of formula $R^1R^2R^3C$—COOH with a 3-6-fold molar amount of epichlorohydrin (ECH) by adding specific amounts of alkali metal hydroxide to the reaction system in three lots and recovering excess ECH before the third reaction step. This patent application is therefore rather typical of the prior art, wherein an excess of ECH is used.

GB 763559 is a very early reference on the preparation of glycidyl esters describing a process for preparing an epoxy ester of a carboxylic acid and a monohydric epoxy alcohol that comprises heating the carboxylic acid with at least two equivalent amounts of an epoxy mono-halogen compound, i.e., ECH, in the presence of a tertiary amine or a quaternary salt or a mixture thereof as a catalyst. As may be expected, a suggestion how to improve the purity at high yield is not provided.

U.S. Pat. No. 2,992,239 provides a method of preparing a glycidyl ester of long chain fatty acids which comprises: forming a mixture comprising a molten fatty acid containing at least ten carbon atoms, an alkali metal carbonate, and a quaternary ammonium halide catalyst in about the mol ratios of 1.0:1.0-1.5:0.0025-0.01, respectively; adding thereto from about 9 to about 13 moles of epichlorohydrin per mol of fatty acid; maintaining resultant mixture at a temperature above the melting point of the fatty acid until reaction substantially ceases, whereby said ester is formed, and recovering product glycidyl ester of said fatty acid from resultant solution. Like the references mentioned before, a suggestion how to improve the purity at high yield is not provided.

CN 1425729 relates to propylenyl pimaric acid diglycidic ester. This reference therefore does not concern the preparation of glycidyl esters of aliphatic branched monocarboxylic acids having at least 5 carbon atoms. The problem of (relatively) low purity and/or low yield is not encountered.

U.S. Pat. No. 6,570,028 describes a process for the manufacture of diglycidyl esters of alpha,alpha'-branched dicarboxylic acids, comprising (a) the reaction of the alpha,alpha'-branched dicarboxylic acid with a halo substituted monoepoxide such as an epihalohydrin, in a 1.1-20 acid equivalent ratio relative to the alpha,alpha'-branched aliphatic dicarboxylic acid. Purities of up to 93% have been achieved. Suggestions as how to improve the purity and yield in the preparation of glycidyl esters of aliphatic branched monocarboxylic acids have not been provided.

In U.S. Pat. No. 3,275,583 epoxy esters are used of the formula $R^1R^2R^3COO(CH_2)_xCR^5/O\backslash CR^6R^7$ (wherein /O\ represents an oxirane ring). These epoxy alkyl esters may be prepared by reacting e.g., monocarboxylic acids and ECH in a stoichiometric ratio, to form a chlorohydrin, which may then be treated with alkaline substances to form the glycidyl ester. In this reference, on the other hand, glycidyl esters are prepared from crude carboxylic acids that have been neutralized with sodium hydroxide. Suggestions on the improvement of the purity and yield are not provided.

DE 1219481 discloses the preparation of glycidyl esters of soap-forming, particularly of dimerised and/or trimerised, fatty acids. They are prepared by the reaction of the appropriate fatty acids with excess epihalohydrin at elevated temperatures (reflux temperature) in the presence of a tertiary amine or a quaternary ammonium salt as catalyst. Products with a purity of up to 84% at a yield of 97% are disclosed (Example 1). Once again, suggestions on the improvement of the purity and yield of a glycidyl ester of a monocarboxylic acid are not provided.

More recently WO 2009/000839 discloses C9 alkanoic acid glycidyl esters and use thereof. According to this process, the acid is reacted with ECH in the presence of a chromium salt. The ECH ratio may be selected from 0.9 to 2 mol, preferably from 1 to 1.5 mol calculated on the acid. The reaction is carried out in solvent (acetonitrile) at 82° C. This reference therefore has the disadvantage that a solvent removal step needs to be included.

Despite the abundance of literature on the preparation of glycidyl esters of branched monocarboxylic acids, and despite the decades of preparation of said esters, the need remains for a simple and improved process that without having to use additional solvents, recycles or purifications steps produces said glycidyl esters in very high purity, i.e., at a purity greater than 93.5%, preferably greater than 94% (which corresponds with an ECG of about 4125 mmol/kg or greater) at a yield greater than 95%, preferably greater than 98%. This aim has been achieved by the process discussed hereinafter.

DISCLOSURE OF INVENTION

Accordingly, the invention relates to a process for the preparation of a glycidyl ester of a branched monocarboxylic acid by reacting an aliphatic monocarboxylic acid of the formula $R^1R^2R^3CCOOH$, wherein $R^1$, $R^2$, and $R^3$ each independently represent an alkyl radical of normal or branched structure containing from 1 to 20 carbon atoms and an epoxyalkyl halide containing from 3 to 13 carbon atoms in the presence of a catalyst, wherein a greater than stoichiometric amount of epoxyalkyl halide is reacted in a coupling reaction with the acid (e.g., preferably in the molar ratio of epoxyalkyl halide to acid that is in the range of from 1.02:1 to 1.50:1) to form an intermediate reaction product comprising a halohydrin, the epoxyalkyl halide is added to the acid with appropriate cooling of the reactants and/or the reaction mixture to keep the temperature of the reaction mixture below 80° C., whereupon the epoxyalkyl halide and the acid are reacted at a temperature below 80° C. (preferably in the range of from 55 to 75° C.) for a time sufficient to reduce the amount of acid to no more than 2 wt % but no less than 0.1 wt % calculated on the initial amount of acid, optionally removing any excess epoxyalkyl halide from the reaction product prior to the ring closure reaction, subjecting the reaction product to a ring closure reaction (DHC) and optionally to one or more after treatments (ADHC) for removal of any remaining halo functionality.

MODE(S) FOR CARRYING OUT THE INVENTION

The carboxylic acid may be an aliphatic, cycloaliphatic, or heterocyclic acid. Preferably, the acid is a secondary or tertiary monocarboxylic acid (or mixture thereof) having one or two alkyl groups linked to the carbon atom that is in the alpha position with respect to the carboxyl carbon atom. Usually mixtures of glycidyl esters of branched monocarboxylic acids are produced, when starting from technical grades of commercially available compositions of α-branched monocarboxylic isomers. These acids may have from 4 to about 20 carbon atoms in the molecule, and include for example pivalic acid, 2-methylbutanoic acid, isobutyric acid, isovaleric acid, 2-methylpentanoic acid, 2,4-dimethylvaleric acid, diethylacetic acid, cyclohexane carboxylic acid. Technical grades of commercially available compositions of a-branched monocarboxylic isomers are preferred starting materials, such as neodecanoic acids, 2-ethyl hexanoic acid or VERSATIC 9 or 10 or 13 acids (VERSATIC is a trademark) as starting materials. Preferably VERSATIC acids having 9 to 11 carbon atoms are used as starting material.

The epoxyalkyl halide is an unsubstituted 1-halo-2,3-epoxyalkane of from 3 to 13 carbon atoms. Preferably it is an epihalohydrin or 2-methylepihalohydrin. The halogen atom preferably is chlorine or bromine. More suitably the epoxyalkyl halide is epichlorohydrin.

It will be appreciated that the glycidyl ester obtained after the last step can be dried in addition e.g. by stripping or treating with water absorbers.

The process according to the present invention can be carried out either as batch process or as a continuous process.

In the coupling reaction of the process of the invention, an additional solvent is not required and preferably is not present. Although solvents have been used in the prior art, as in WO 00/17179 discussed above, the use of a solvent has an adverse impact on the overall economics of the process. Thus, the energy to distil, remove and/or purify the solvent is basically wasted.

The catalyst to be used in the process of the present invention is preferably a homogeneous catalyst that does not require a solvent. The catalyst may be selected from the catalysts known in the prior art. Thus it may be selected from alkalimetal hydroxides, alkalimetal carbonates, alkaline earth hydroxides, alkalimetal or alkaline earth metal alcoholates, or ammonium salts and in particular hydroxides or halides of the formula $R'R''R'''R''''N^+Y^-$, wherein R', R" and R'" independently of each other may represent an alkyl group having from 1 to 16 carbon atoms, which optionally may be substituted with one or more hydroxyl groups, wherein R" represents an alkyl group having from 1 to 16 carbon atoms, phenyl or benzyl, and wherein Y represents hydroxyl or halogen, such as chlorine, bromine or iodine. Also the corresponding phosphonium salts and aromatic versions thereof like ethyl triphenyl phosphonium iodide may be used.

Preferred catalysts during the coupling reaction are ammonium salts and in particular hydroxides or halides of the formula $R'R''R'''R''''N^+Y^-$, wherein R1, R2 and R3 independently of each other may represent an alkyl group having from 1 to 10 carbon atoms, and Y represents chlorine or bromine. Most preferred catalysts are tetramethyl ammonium chloride or bromide (TMAC or TMAB).

Most importantly, the temperature is kept low during the epoxyalkyl halide addition and during the subsequent reaction, whereas the coupling reaction is continued for a time sufficient to reduce the amount of free acid to less than 2 wt %. The inventors found that if more free acid is present during the subsequent ring closure reaction, than various by-products are produced. On the other hand, if the reaction is allowed to proceed to more than 0.1 wt % completion, the inventors found that some of the intermediate halohydrin is already converted into by-products. The conversion of the halohydrin appears to be an effect of the reaction temperature during the epoxyalkyl halide addition and the coupling reaction itself, which is an exothermic reaction. Thus, by keeping the temperature low, i.e., below 80° C., and preferably below 75° C. and more preferably at or below 70° C., the production of by-products is significantly avoided. On the other hand, the temperature should at least be ambient, to allow the reaction to start. More preferably the temperature is at least 55° C., more preferably at least 60° C. to obtain reasonable conversion rates. The temperature may be controlled by internal cooling and external cooling of the reaction mixture and/or by addition of pre-cooled epoxyalkyl halide. Although the epoxyalkyl halide may be added as batch, for temperature control reasons it is preferred to add the reactant either in multiple steps, e.g., in small amounts, or continuously, and then preferably at small addition rates.

At least a stoichiometric amount of epoxyalkyl halide is to be used. Higher than stoichiometric amounts have the advantage of accelerating the reaction. On the other hand, once the coupling reaction has been completed, any residual epoxyalkyl halide is waste and a source of by-products and impurities in the subsequent ring closure reaction. Thus it is preferred to remove substantially all of the remaining epoxyalkyl halide prior to the ring closure reaction. The epoxyalkyl halide may be removed, e.g., by distillation or similar methods. More preferred, however, is to keep the epoxyalkyl halide very close to the stoichiometric amount. Thus, the amount of epoxyalkyl halide is preferably used in a molar ratio of epoxyalkyl halide to acid that is greater than 1, e.g., at least 1.01, more preferably at least 1.02, but no greater than 1.5, more preferably no greater than 1.2, still more preferably no greater than 1.1.

Crucial in this coupling reaction step is the degree of conversion of the acid into the halohydrin, which is a function of the reaction temperature, the ratio of the reactants and of the duration of the coupling reaction step. As mentioned, the acid should be converted to the extent that the no greater than 2 wt % of acid, preferably no greater than 0.65 wt % of acid remains. The reaction should be terminated before full completion, i.e., before the amount of remaining acid drops below 0.1 wt %, preferably before the amount of remaining acid drops below 0.3 wt %. When reducing the acid to residual levels within the range of 2 to 0.1 wt %, then it is possible to produce glycidyl esters with an EGC of about 4100 mmol/kg or better in high yield. When reducing the acid to residual levels within the preferred range of from 0.65 to 0.3 wt %, then an EGC of about 4135 mmol/kg or better can be achieved, again in a yield of 95% based on the acid. This presupposes an appropriate temperature control as defined above and the removal of about all epoxyalkyl halide before starting the ring closure reaction. The degree of conversion can be easily monitored using various online techniques or by analysing samples taken from the reaction mixture.

In a typical lab set up, on a 2 liter scale with internal and external cooling, the addition of epoxyalkyl halide may be carried out within a relatively short time span of about 30 minutes. The preferred degree of conversion, using near stoichiometric amounts of reactants may then be achieved in 2 to 6 hours. On a commercial scale, appropriate cooling may be more difficult; the addition step of the epoxyalkyl halide may take from about 30 minutes to 5 hours, whereas the desired conversion may take from 4 to 12 hours.

As mentioned above, the process involves two steps; a coupling reaction and a ring closure reaction to convert the intermediate halohydrin into the desired glycidyl ester.

This second step of the process may be performed in a manner similar to that used in the prior art. Thus, in ring closure reactions known from the art preferably relatively strong and water-soluble metal hydroxides or metal alcoholates are used. This so-called DHC reaction may be performed by addition of alkali metal hydroxide or alkali metal alkanolate. The reaction is preferably carried out at a temperature of from 50 to 90° C., and more preferably from 60 to 80° C. Suitably, the reaction is completed within a period of from 40 to 300 minutes. However, this again depends on the scale of the reaction.

During this second step of the process the inventors found that various by-products may be produced and various impurities may be collected within the final product. The production of these by-products and impurities may be reduced when keeping to the conditions in the coupling reaction step as defined above.

According to a preferred embodiment of the present invention the brine formed during the ring closure reaction can be completely or partially removed, whereupon the product may be subjected to the optional after treatment.

The optional after treatment may be performed by methods known in the art. The effect of this after treatment is that the halogen content is effectively reduced.

The alkali metal hydroxide or alkali metal alkanolate that may be used in the above steps for DHC and the ADHC is preferably selected from sodium hydroxide or potassium hydroxide, a sodium alkanolate having from 1 to 6 carbon atoms, such as sodium isopropanolate, or potassium alcoholate. Most preferably sodium hydroxide or sodium alkanolate having from 1 to 6 carbon atoms is used.

In these steps sodium hydroxide is preferably used in an aqueous solution of a concentration of from 15 to 60% by weight and more preferably from 20 to 50% by weight. It will be appreciated that according to the process of the present invention a drying step can take place after the final washing step, if desired.

It has surprisingly been found, that the process of the present invention can provide very pure glycidyl esters of branched monocarboxylic acid, i.e. showing contents of heavier by-products less than 6 wt % and preferably less than 5 wt % and more preferably less than 4 wt %, which show the desired improved purity, and which do not need tailing by e.g. distillation for purification, while the process can be further characterized by a very high conversion higher than 98% (based on starting carboxylic acid) and selectivity of the halo substituted epoxide with reference to the desired glycidyl ester.

The following experiments illustrate the current invention. The following abbreviations are used:
ECH: Epichlorohydrin
TMAC: Tetramethylammonium chloride
V10: Versatic 10 acid, (tm by Hexion of neodecanoic acid)
EGC: Epoxy Group Content.

Epoxy Group Content (EGC) (ISO 3001)

The analysis is performed as follows. Weight a test portion (0.1-0.5 g) of the glycidyl ester to the nearest 0.1 mg into a 150 ml beaker. Add 25 ml of a 4/1 mixture of dichloromethane (DCM) and glacial acetic acid (AA) and dissolve the test portion by stirring. Whilst stirring, add 2.0±0.1 g of acetyl trimethyl ammonium bromide and 4 drops of crystal violet indicator solution (100 mg indicator in 100 ml AA). Titrate with standard acetous perchloric acid, $HClO_4$ (0.1N) from blue (via blue-green) to an emerald green end-point. The quantity of acetous perchloric acid consumed is a measure of the epoxy group content.

The EGC may be calculated as follows:

$$EGC = 100 \times 1000 \times N \text{ times } (V1-V0) \text{ divided by } m1 \times NV$$

where
EGC=epoxy group content, mmol/kg
V0=volume of $HClO_4$ solution used for the blank test, ml
V1=volume of $HClO_4$ solution used for determination, ml
N=normality of $HClO_4$
m1=mass of the test portion, g
NV=the non-volatile matter content, determined according to ISO 3251, % m/m.

Accurate results can be obtained by use of automatic titration equipment.

The purity may be calculated by dividing the EGC by the theoretical EGC times 100%.

The yield is calculated on the mol product, divided by the mol fatty acid originally used, times 100%.

Manufacturing Procedure

Experiments were carried out on different scales. By way of example, the experiment on a lab scale is described in detail. As equipment a lab reactor, provided with a mechanical stirrer, heating jacket and a connection to a distillation column were used.

EXAMPLE 1

Lab Scale 861 grams (5 mol) V10 and 44 grams (0.04 mol/mol acid) TMAC (as 50% aqueous solution) were charged to the reactor and heated to 73° C., switch off heating. Next ECH was dosed to the reactor while cooling the reaction medium to about 70° C. The addition rate was kept low to allow for appropriate cooling. In total 500 grams ECH were added over a period of about 5 hours (1.08 mol/mol acid). The addition time is hence a function of the cooling efficiency.

While keeping the reaction at about 70° C. the reaction was allowed to proceed until the acid content was reduced to about 0.3 wt %. The reaction was monitored and at the present conditions this took about 5 hours.

The product was analyzed. The residual ECH was about 1 wt %. Together with the formed dichlorohydrin (about 2.5 wt %) it covers the excess of ECH in the recipe. The presence of ECH and DCH will result in the formation of glycerine during the ring closure reaction, but this may be removed without to much trouble with the brine.

The ring closure reactions were performed in the presence of caustic at 70° C. In total 126.6 g NaOH (1.4 mol/mol V10) was used. The NaOH was dosed, using a linear profile. Upon completion of each ring closure reaction the product was washed with water. After a final wash and filtering the EGC of the end product was analyzed and found to be 4139 mmol/kg (purity 94.4%). The yield in mol product per mol V10 was 99.2%.

These results clearly show that the thermosetting powder compositions in according with the invention have advantageous characteristics compared to those obtained from compositions of the prior art (Comparative examples I, L and M).

EXAMPLE 2

Bench Scale

The reaction was performed in a manner similar to example 1, albeit at a different scale. Thus 8017 grams (46.6 mol) V10 was used. TMAC (as 50% aqueous solution) was used in an amount of 409 grams (0.04 mol/mol acid). ECH was used in an amount of 4658 grams (1.08 mol/mol acid).

The temperature was kept both during the ECH addition and the post reaction to about 70° C. The dosing took about 5 hours. The post reaction, to achieve an acid content of about 0.3 wt % likewise took about 5 hours.

In total 2674 g NaOH (1.4 mol/mol V10) was used in the ring closure reaction. After a final wash and filtering the EGC of the end product was found to be 4140 mmol/kg. The yield in mol product per mol V10 was 98.5%.

EXAMPLE 3

Plant Scale

The reaction was performed in a manner similar to example 1, albeit at a different scale. Now 5906 kilograms (34.3 kmol) V10 was used. The amount of TMAC (as 50% aqueous solution) was 310 kilograms (0.04 mol/mol acid). The amount of ECH was 3433 kilograms (1.08 mol/mol acid).

The temperature was kept both during the ECH addition and the post reaction to about 70° C. The dosing took about 5 hours. The post reaction, to achieve an acid content of about 0.3 wt % now took about 6 hours.

In total 2070 kg NaOH (1.5 mol/mol V10) was used in the ring closure reaction. After a final wash and filtering the EGC of the end product was 4133 mmol/kg. The yield in mol product per mol V10 was 98.1%.

COMPARATIVE EXAMPLE 1

Lab Scale

The experiment was carried out exactly as described in CN101245053, using the equipment described above.

Thus, ECH and catalyst are charged to the reactor and heated to 90° C. V10 is added to the reactor and the addition rate is controlled to maintain the temperature at 90° C. (about 0.5 hours). During the subsequent post reaction, the acid content was analyzed. After half an hour, the acid content was 18.85 wt %. According to the CN reference, this should be less than 0.16 wt %. However, even after 360 minutes, the acid content was 18 wt %. At the end of this reaction already a significant amount of diester could be identified. This increased from 2.53 wt % after 30 minutes of post reaction to 5.26 wt % after 360 minutes. Clearly, this reference did not provide the improvement in terms of purity and efficiency that was promised in the patent specification.

CONCLUSIONS

Careful control of the reaction temperature (and thus dosing regime of the ECH) in combination with a careful control of the conversion of the acid into the halohydrin intermediate product results in a glycidyl ester having a high EGC at a high yield based on the starting acid.

Increase of the reaction temperature results in the formation of by-products. Likewise, by-products are formed if the coupling reaction is terminated too soon or too late.

Addition of the acid to a mixture of ECH and catalyst has no advantages. Also from a safety perspective this manner of performing the reaction is undesirable. Indeed, ECH is rather unstable and flammable with wide explosion limits and low flash point.

Using ECH at elevated temperatures and adding the acid thereto is therefore more risky then adding ECH to the acid.

INDUSTRIAL APPLICATION

The glycidyl esters may be used as an intermediate for the manufacture of resins and polymers and for different chemical syntheses via reactions with its epoxide group. Its characteristics and properties make them attractive for a wide variety of paint applications, particularly those based on polyesters, acrylics and epoxy resins. They may also be used as a reactive diluent for epoxy resins based on bisphenol A, bisphenol F or blends of these two.

We claim:

1. A process for the preparation of a glycidyl ester of a branched monocarboxylic acid comprising reacting an aliphatic monocarboxylic acid of the formula $R^1R^2R^3CCOOH$, wherein $R^1$, $R^2$, and $R^3$ each independently represent an alkyl radical of normal or branched structure containing from 1 to 20 carbon atoms and an epoxyalkyl halide containing from 3 to 13 carbon atoms in the presence of a catalyst, wherein
epoxyalkyl halide is reacted with the aliphatic monocarboxylic acid in a molar ratio of epoxyalkyl halide to aliphatic monocarboxylic acid of greater than 1 to 1.5 in a coupling reaction to form an intermediate reaction product comprising a halohydrin,
the epoxyalkyl halide is added to the aliphatic monocarboxylic acid with cooling of the reactants or the reaction mixture to keep the temperature of the reaction mixture from 55° C. to below 80° C., such that the epoxyalkyl halide and the aliphatic monocarboxylic acid are reacted at a temperature from 55° C. to 80° C. for a time sufficient to reduce the amount of aliphatic monocarboxylic acid from 0.1 wt % to 2 wt % calculated on the initial amount of aliphatic monocarboxylic acid,
retaining unreacted epoxyalkyl halide in the reaction product by the absence of distillation; and then
subjecting the reaction product to the ring closure reaction, wherein the catalyst is selected from the group consisting of alkali metal hydroxides, alkali metal carbonates, alkaline earth hydroxides, alkali metal, alkaline earth metal alcoholates, ammonium salts, and phosphonium salts.

2. The process of claim 1, wherein a molar ratio of epoxyalkyl halide to aliphatic monocarboxylic acid is from 1.01 to 1.08.

3. The process of claim 2, wherein the molar ratio of epoxyalkyl halide to aliphatic monocarboxylic acid is from 1.01 to 1.02.

4. The process of claim 1, wherein unreacted epoxyalkyl halide is removed before the ring closure reaction.

5. The process of claim 1, wherein the reaction temperature of the coupling reaction during and after the addition of the epoxyalkyl halide is from 55° C. to 75° C.

6. The process of claim 1, wherein the reaction temperature of the coupling reaction during and after the addition of the epoxyalkyl halide is from 60° C. to 70° C.

7. The process of claim 1, wherein the coupling reaction is continued until the amount of aliphatic monocarboxylic acid is from 0.3 wt % to 0.65 wt %.

8. The process of claim 1, wherein the aliphatic monocarboxylic acid is an aliphatic tertiary alpha-branched monocarboxylic acid or a mixture thereof.

9. The process of claim 8, wherein the aliphatic tertiary alpha-branched monocarboxylic acid has two alkyl groups linked to the carbon atom that is in the alpha position with respect to the carboxyl carbon atom.

10. The process of claim 9, wherein the aliphatic tertiary alpha-branched monocarboxylic acid has from 4 to about 20 carbon atoms.

11. The process of claim 1, wherein the epoxyalkyl halide is an epihalohydrin or a 2-methylepihalohydrin.

12. The process of claim 11, wherein the epoxyalkyl halide has a chlorine or bromine atom.

13. The process of claim 1, carried out in the absence of an additional solvent.

14. The process of claim 1, wherein a homogeneous catalyst is used in the coupling reaction that does not require a solvent.

15. The process of claim 14, wherein the catalyst comprises alkali metal hydroxides or alkali metal alkanoates.

16. The process of claim 15, wherein the catalyst is selected from ammonium hydroxides or halides of the formula R'R''R'''R''''N$^+$Y$^-$, wherein R', R'' and R''' independently of each other may represent an alkyl group having from 1 to 16 carbon atoms wherein R'''' represents an alkyl group having from 1 to 16 carbon atoms, phenyl or benzyl, and wherein Y represents hydroxyl or halogen.

17. The process of claim 1, wherein the process has no purification steps under pressure at the end of ring-closure reaction.

18. The process of claim 1, further comprising removing epoxyalkylhalides as glycerine during the ring closure reaction.

19. The process of claim 16, wherein the alkyl group may be is substituted with one or more hydroxyl groups.

20. The process of claim 9, wherein the aliphatic tertiary alpha-branched monocarboxylic acid is a mixture of aliphatic tertiary alpha-branched monocarboxylic acids.

* * * * *